United States Patent [19]
Carlson

[11] 4,112,927
[45] Sep. 12, 1978

[54] ULTRASONIC DETECTOR WITH AUDIBLE INDICATION SIGNAL

[75] Inventor: David L. Carlson, Ames, Iowa

[73] Assignee: Renco Corporation, Minneapolis, Minn.

[21] Appl. No.: 785,174

[22] Filed: Apr. 6, 1977

Related U.S. Application Data

[63] Continuation of Ser. No. 637,825, Dec. 4, 1975, abandoned.

[51] Int. Cl.² ............................................. A61B 10/00
[52] U.S. Cl. ........................................ 128/2 V; 73/597; 73/614
[58] Field of Search ............ 128/2 V, 2.05 Z, 2.06 A, 128/24 A; 73/67.7–67.9, 597, 614

[56] References Cited

U.S. PATENT DOCUMENTS

| | | | |
|---|---|---|---|
| 3,041,872 | 7/1962 | Brown et al. | 73/67.9 |
| 3,053,080 | 9/1962 | Colten et al. | 73/67.9 |
| 3,555,889 | 1/1971 | Weighart | 73/67.9 |
| 3,565,057 | 2/1971 | Hart | 128/2.05 Z |
| 3,828,768 | 8/1974 | Douglas | 128/2.06 A |
| 3,872,858 | 3/1975 | Hudson et al. | 128/2 V |
| 3,888,238 | 6/1975 | Meindl et al. | 128/2 V |
| 3,921,622 | 11/1975 | Cole | 128/2 V |
| 3,972,228 | 8/1976 | Mansson | 73/67.7 |

Primary Examiner—Lee S. Cohen
Attorney, Agent, or Firm—Merchant, Gould, Smith, Edell, Welter & Schmidt

[57] ABSTRACT

A pulsed ultrasonic detection system particularly adapted for detection of biological tissue includes a probe for placement against the body, apparatus for transmitting ultrasonic energy into the body and for receiving return pulses, signal processing circuits and a cathode ray tube display for displaying the return pulses as a function of time. A gating signal is generated after a predetermined time delay from each transmitted pulse, and the time delay and the duration of the gating signal are selected to correspond to the timing of a particular expected return pulse. Return pulses are gated into an audible signal device by a switching device, but only during the time interval thus defined by the gating signal. If a return pulse of sufficient amplitude occurs during the gated interval, the audible signal device is energized.

11 Claims, 3 Drawing Figures

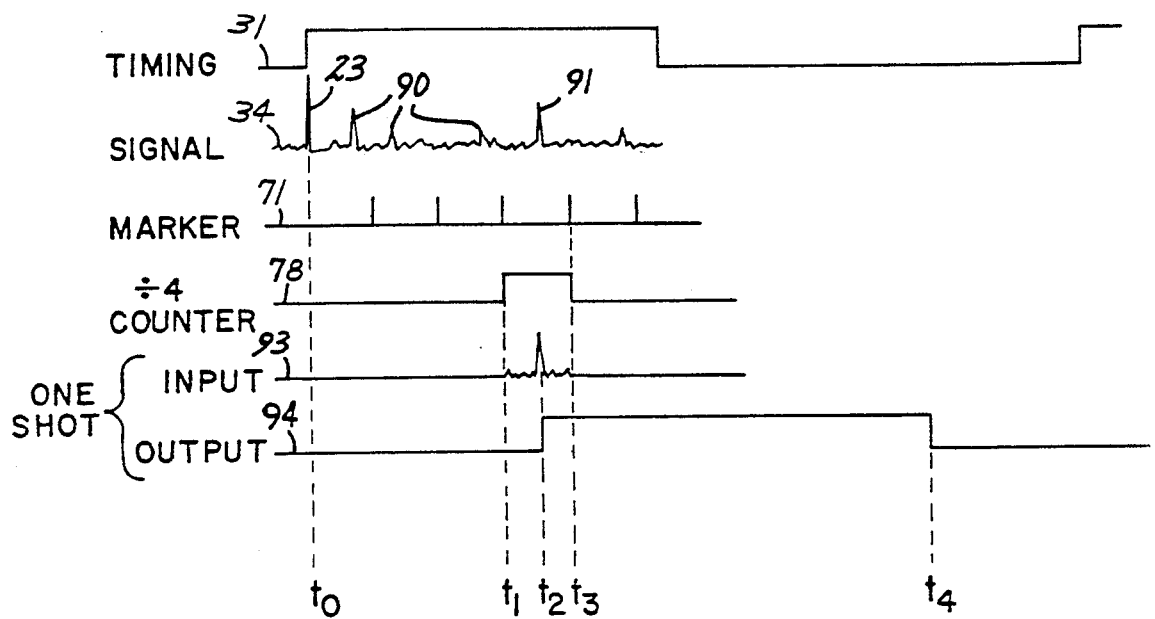
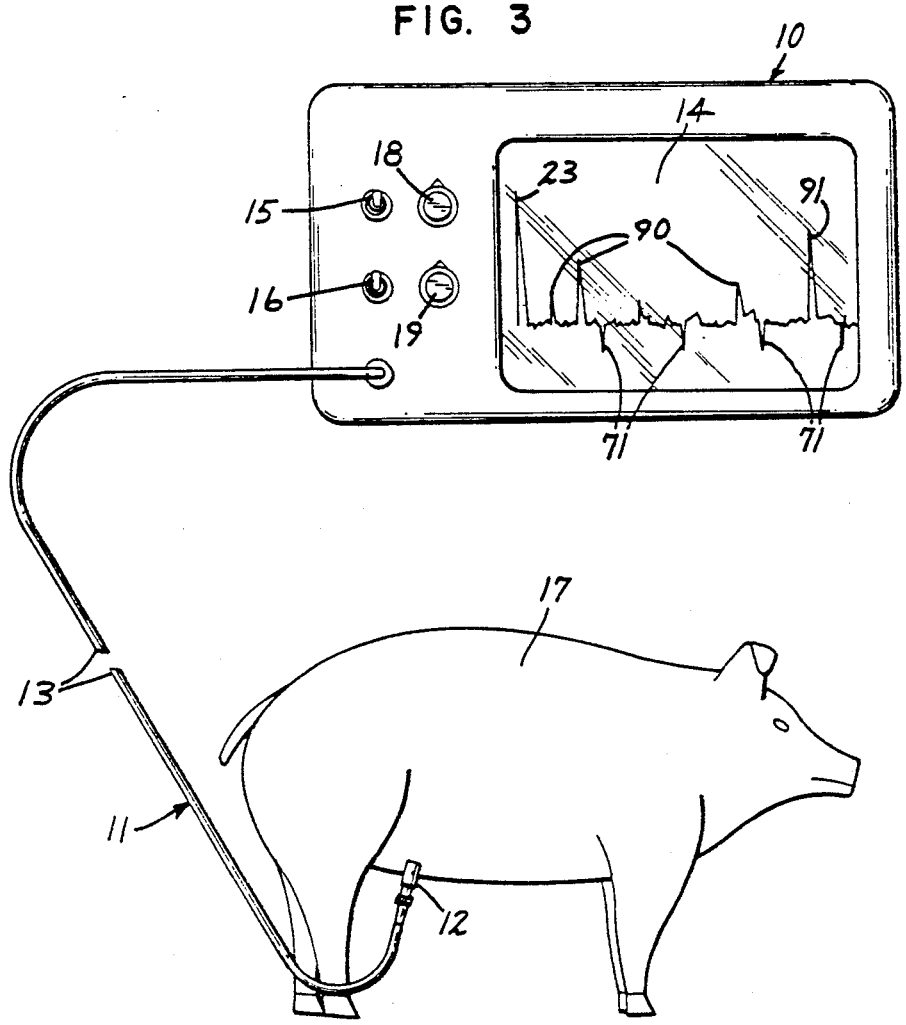

ULTRASONIC DETECTOR WITH AUDIBLE INDICATION SIGNAL

This is a continuation of application Ser. No. 637,825, filed Dec. 4, 1975, now abandoned.

BACKGROUND OF THE INVENTION

The present invention relates to ultrasonic detection apparatus, and in particular to the field of biological detection using ultrasonic apparatus.

Ultrasonic detection has been used in a number of prior art systems for measuring or detecting physiological data within a body, either human or otherwise, by means of ultrasonic transducers external of the body. Such systems take advantage of the fact that pulses of ultrasonic energy propagated into the body will echo or reflect from various internal organs or boundaries of differing tissue structures. From a knowledge of the velocity at which the pulses are propagated in the body, it is possible to deduce the position of a particular internal portion of the body by observing the timing of the return pulse reflected from that body structure. This method has been used for example, in detecting dislocations of the brain in cases of severe head injuries.

Another use of this general method has been in the field of animal husbandry, in which ultrasonic pulsing and detection has been used for detecting pregnancies in sows and other farm animals. For many reasons it may be economically important for a livestock producer to know if individual farm animals may be pregnant. For example, such knowledge may be required in order to make a decision of whether to market the animal; whether to start it on a special feeding program; or whether to re-breed the animal during the same season.

It has been found in the prior art that an ultrasonic echo or return pulse is much stronger from the uterus of a pregnant animal than from one which is not pregnant, thus providing a basis for testing. The strong return is from the build up of amniotic fluid in the enlarged uterus which occurs during the gestation period, some time following conception. For example, in the case of sows, the build up is usually sufficient after about thirty days following conception to give a positive indication via ultrasonic detection.

One successful type of prior art ultrasonic detector for use in livestock pregnancy detection has used a cathode ray tube for displaying the echoes or return pulses received from within the animals body. The trace is swept horizontally as a function of time, while the return pulse pattern is traced out vertically. With suitable instruction, an operator can learn to interpret the traces to look for a pulse of sufficient amplitude at a given time delay from the transmission of the pulse, which signifies a pregnant condition in the animal being tested. However, each layer of skin, fat and bone, and numerous other organs will return echoes, giving rise to a multitude of spikes on the CRT display. It thus takes certain amount of training and experience, together with a certain minimum amount of time to study the oscilloscope trace in order for the operator to make the determination. Unfortunately, while the operator is trying to study the oscilloscope pattern, the animal under observation may try to squirm away from the probe placed at her belly, or at worst she may be trying to attack the probe and/or its operator. It therefore demands nearly the full attention of the operator just to maintain the probe in position, making it very difficult at best for an operator to place the probe, restrain the animal, and study the oscilloscope display.

The present invention adds to this prior art type of ultrasonic detection system by providing an automatic audible indication circuit. Through the use of the present invention, the operator is only required to position the probe on the animal, then listen for the signal tone. The presence of a tone indicates the strong return signal from the uterus, while the absence of a tone indicates that the animal is not pregnant. It is therefore only necessary to look at the oscilloscope display for marginal cases or unusual situations for example involving disease; alternatively, an experienced and knowledgeable operator can still use the display to obtain subtle, quantitative data concerning the returns, if necessary.

SUMMARY OF THE INVENTION

According to the present invention there is provided an ultrasonic detection apparatus having an audible signalling device for automatically detecting the presence or absence of a particular expected return pulse. Means are provided for generating and transmitting ultrasonic energy pulses into the animal and for receiving return pulses from the animal, by means of a probe for placement against the animal's body. Display means including a cathode ray tube are provided for displaying the return pulses as a function of time. Circuits are provided for generating a gating signal which commences after a predetermined time delay following the transmission of a pulse and continuing for a predetermined time interval. The time delay and the time interval of the gating signal are selected to correspond to the normal range of values of the expected return pulse. A switching means is operated in response to the gating signal, and functions to transmit received return pulses to an audible signal generating device, but only during the interval in which the gating signal is present. The audible signal device generates an audible signal in response to a received return pulse of a predetermined amplitude. In this manner, an audible signal is generated only if a return pulse having sufficient amplitude is received within the defined timing interval corresponding to the distance of depth of the organ or body portion to be detected.

BRIEF DESCRIPTION OF THE DRAWINGS

In the drawing,

FIG. 2 is a timing diagram illustrating the operation of the circuit of FIG. 1; and FIG. 3 is a pictorial diagram illustrating the operation of the detector of FIG. 1.

DESCRIPTION OF THE PREFERRED EMBODIMENT

Figure 1:
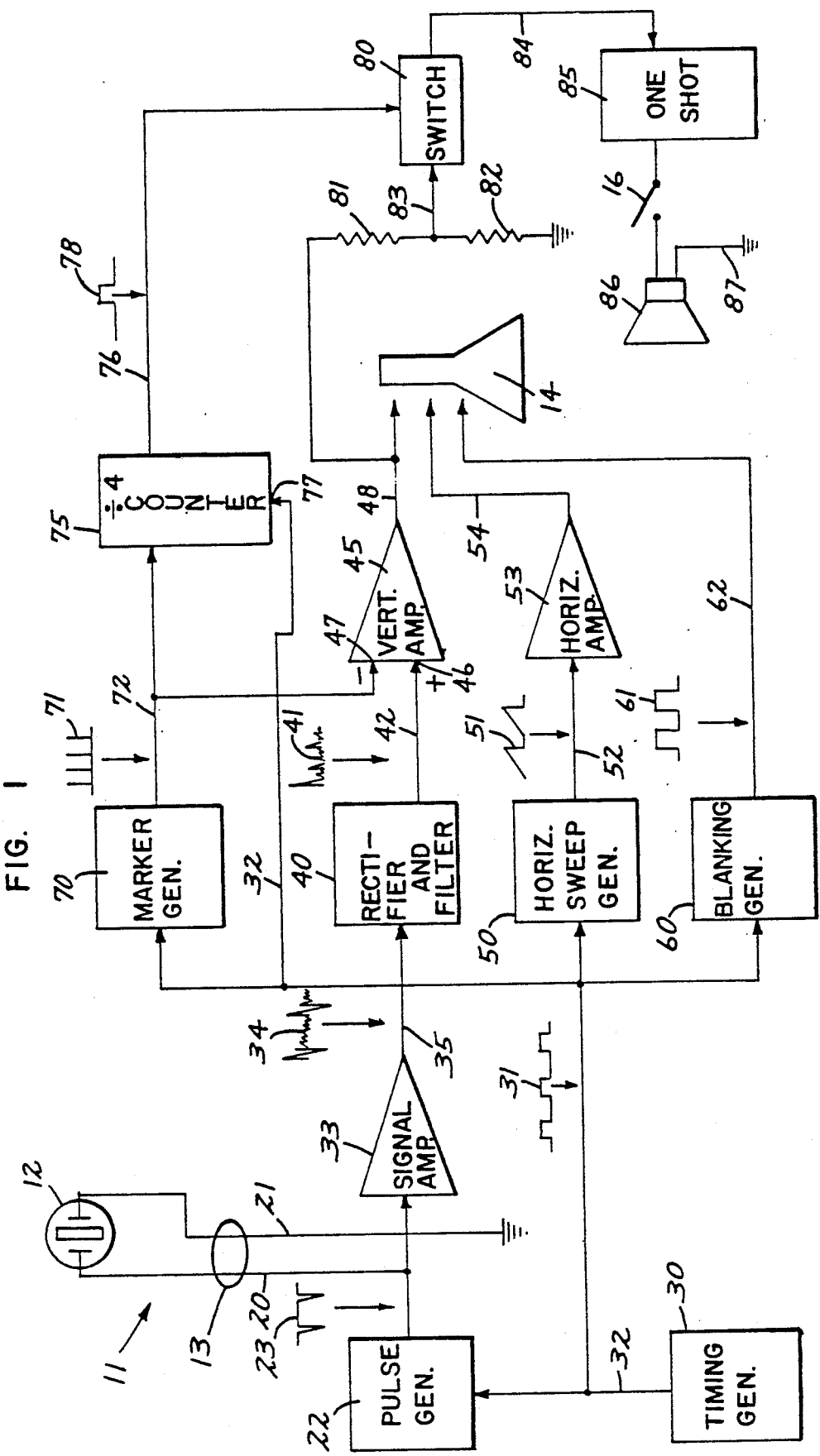
FIG. 1 is a block diagram of an ultrasonic detection apparatus incorporating the present invention.

For purposes of illustration, a preferred embodiment of the present invention will be described as it is applied to an ultrasonic pregnancy detector for sows. It will be appreciated that the present invention is equally adaptable to detection of a number of different body organs or areas, both in humans and in animals, by suitable selection of timing an amplitude parameters, according to the depth and body of, and magnitude of return pulse from, the body organ or area to be detected.

Referring to FIG. 3, the detection apparatus of the present invention includes a portable instrument housing generally designated by reference numeral 10, and a probe assembly generally designated by reference numeral 11. The probe includes an ultrasonic transducer 12 which is connected by means of an electrical cable 13 to a suitable connector on the front panel of the instrument. The instrument also includes on its front panel the face of a cathode ray tube or oscilloscope 14. A power switch 15 is provided for turning off and on the instrument, and a second switch 16 is provided for enabling or disabling the audible tone detection feature of the present invention. Display control knobs 18 for depth and 19 for sensitivity are also provided as explained hereinafter.

Referring now to the functional electronic block diagram of FIG. 1, the circuit of the preferred embodiment of the present invention will now be described. It should be noted that in addition to the circuitry shown, the system includes a power supply which in the preferred embodiment is a rechargeable battery, so that the instrument can be truly portable and can be taken to the location of the animals for use without the necessity of providing electrical power outlet nearby. The DC potential from the battery can supply most of the circuits, but inverters and rectifier circuits will be necessary to provide the higher DC voltages required for the cathode ray tube and the vertical and horizontal amplifiers. Since these circuits are well known in the art, they have been omitted from FIG. 1 for purposes of clarity.

In FIG. 1, ultrasonic transducer 12 is shown connected via cable 13 to the rest of the circuitry. Specifically, one side of transducer 12 is connected to a lead 20, and the other side is connected to a lead 21 which connects to signal ground. In the preferred embodiment, the transducer 12 is a piezoelectric crystal having a resonate mode at a frequency of 2mHz. A pulse generator circuit 22 has its output connected to lead 20 for driving the transducer. In the preferred embodiment the pulse generator may comprise a capacitor discharge circuit using an SCR, to provide output pulses of minus 50 volts with a duration of one microsecond, so as to excite the resonate mode of the transducer. The output wave form from the pulse generator is suggested by wave form 23.

The firing of pulse generator 22 is controlled by a timing generator 30, which provides at its output on lead 32, master timing pulses as suggested by waveform 31. Timing generator 30 may be for example a free running multivibrator and in the preferred embodiment, it is a integrated circuit type NE 555 adjusted to produce an output period of one millisecond.

Lead 32 from the timing generator output connects to a trigger input on pulse generator 22, and generator 22 operates to produce a pulse for each master timing pulse from generator 30. Thus, the pulses delivered to transducer 12 come at one millisecond intervals. These pulses cause the piezoelectric transducer 12 to emit a pulse of ultrasonic energy. Return pulses impinging on the transducer generate voltages on lead 20, and these are fed into the input of a signal amplifier 33 for amplification. Amplifier 33 may be any type of signal amplifier, for example in the preferred embodiment it is a three stage FET amplifier, having a gain of approximately 1,000. Amplified return pulse signals as suggested by reference numeral 34 are fed from the output of signal amp 33 by means of a lead 35 to a rectifier and filter circuit 40. Circuit 40 comprises a halfwave rectifier for producing only a single polarity of return pulse signal, as suggested by waveform 41. The circuit also includes an RC filtering circuit for rolling off the high frequency response so as to damp the inherent resonate ringing quality of the return pulses which are due to the characteristics of the transducer 12. The rectifier and filter circuit 40 thus produces a sharp single polarity pulse for each echo received. These pulses are delivered from the output of circuit 40 to a lead 42 to the noninverting input 46 of the vertical deflection amplifier 45. Here the signals are summed against marker pulses as explained hereinafter, and the composite signals are amplified to a suitable potential, and are applied through a lead 48 to the vertical deflection circuits of the cathode ray tube (CRT) 14.

The master timing pulses 31 are also connected to the input of a horizontal sweep generator 50, which functions to produce ramp pulses as suggested by waveform 51, for controlling the horizontal sweep of the CRT. These ramp pulses are fed by a lead 52 to the horizontal deflection amplifier 53, where they are amplified to sufficient voltage to deflect the CRT electron beam. The output of horizontal deflection amplifier 53 connects by means of a lead 54 to the horizontal deflection inputs of CRT 14.

The master timing pulses 31 are also fed via lead 32 to a blanking generator 60, which functions to produce at its output blanking signals as suggested by waveform 61. These signals are connected by means of a lead 62 to the brightness control input of CRT 14. The purpose of the blanking generator is to turn on the brightness of the electron beam during a trace of the beam in which the return pulses are being displayed, and to blank out the beam inbetween traces.

The master timing pulses are also applied via lead 32 to a marker generator 70. This generator produces a series of short pulses in response to the initiation of a master timing pulse. Thus, when timing generator 30 goes positive, or to a logical one, at the beginning of a timing cycle, marker generator 70 begins to remit a series of pulses as suggested by waveform 71. When the timing generator returns to its zero state during the latter portion of the timing cycle, the marker generator is inhibited. In the preferred embodiment, the marker generator is a unijunction transistor oscillator in which an input RC circuit is selected to provide the desired frequency of the marker pulses 71. These marker pulses are fed on a lead 72, to the inverting input 47 of the vertical deflection amplifier 45. In this manner, the vertical deflection amplifier produces a composite output signal in which the return signals (echoes) show as upward deflections of the beam, and the marker generator pulses cause strong downward deflections at regularly spaced intervals along the sweep. The marker pulses are thus used for distance measuring where interpreting the readings on the face of the CRT, as explained hereinafter.

The marker pulses 71 are also transmitted to the input of a divide by four digital counter 75. This circuit may be a commercially available digital integrated circuit with suitable connections so that the output connected to the lead 76 goes to a logical 1 when the counter reaches its fourth counting state. Lead 32 from the timing generator also connects to a reset input 77 on the divide by four counter. Thus, on the initiation of a master timing pulse, counter 75 is reset to zero from whatever count it may have previously contained, and shortly thereafter it begins to count up the marker pulses 71 generated by marker generator 70. After the third such pulse is received, the counter is in its fourth state and an output voltage appears at lead 76, but is removed after the fourth and succeeding pulses are received.

The output signal at lead 76 thus represents a gating pulse which comes on after a predetermined time delay following the initiation of a master timing cycle, and stays on for a predetermined time interval, under control of the marker generator 70 and the divide by four counter 75. This gating pulse, as suggested by waveform 78 is connected to control an electronic switch 80. Lead 48 from the output of vertical deflection amplifier 45 connects through series resistors 81 and 82 to signal ground. From their junction, a lead 83 connects to switch 80. The output from switch 80 connects on a lead 84 to the input of a monostable multivibrator, or one-shot, circuit 85. One-shot 85 is selected in the preferred embodiment to have an on-time of one-half millisecond. The output from one-shot 85 connects through switch 16 to a loudspeaker 86, and the circuit to ground is completed by a lead 87.

The detailed operation of the circuit of FIG. 1 will now be explained with reference to the timing diagram of FIG. 2. In FIG. 2, the horizontal axis represents time and the vertical axis voltage amplitude or relative logic signal level. A number of the waveforms indicated in abbreviated form in FIG. 1 are shown more precisely in FIG. 2, in expanded horizontal scale. The timing pulses 31 are indicated in the top waveform of FIG. 2. As previously stated, these pulses control the operation of the entire device. At time $t_0$, a master timing pulse is initiated by the waveform 31 going to its higher potential or logical one state. This causes pulse generator 22 and transducer 12 to emit a burst of ultrasonic energy.

The received return pulse signal, as amplified by amplifier 33 is indicated by waveform 34. Since amplifier 33 is directly coupled to the transducer, the initial pulse appears as time $t_0$. Thereafter over the next several hundred microseconds, a number of peaks or strong echoes are detected, as indicated by reference numeral 90. These echoes represent signal returns from various skin and fat layers, bones and other internal body organs. Since these represent returns from distinct and major body components, they stand out in amplitude above the general "noise" level of the return signal. Waveform 34 shows another sharp return pulse 91 occurring at about 300 microseconds from the initial pulse. This pulse, if of sufficient magnitude as shown in FIG. 2, represents a strong return from the uterus confirming that a pregnancy condition exists in the animal in the test.

After time $t_0$, marker generator 70 begins producing its series of pulses as indicated by waveform 71. After the third such pulse, the output of counter 75 goes positive for one count, then returns to its off state, as indicated by waveform 78 in FIG. 2. The pulse thus generated at waveform 78 represents the gating signal which is used to allow pulses to pass through the audible signalling device which is made up of the switch 80, one-shot 85 and speaker 86.

During the ON period of waveform 78, from time $t_1$ to $t_3$ in FIG. 2, switch 80 of FIG. 1 is enabled, so that whatever return pulses occur during this time interval, are allowed to pass through lead 83, switch 80 and lead 84 to the one shot circuit 85.

Whether or not one shot circuit 85 will be triggered depends upon the magnitude of the input pulse (if any) applied to its input. The actual voltage required to trigger the one shot of course depends upon the individual circuit design and characteristics of the particular one shot circuit employed. Accordingly, resistors 81 and 82 are employed to comprise a voltage divider network. By proper selection of the values of these resistors, the sensitivity of one shot 85 is in effect adjusted, so that it will not be triggered by noise or weak returns, but will be triggered by a strong return pulse indicating a pregnancy condition.

In FIG. 2, reference numeral 93 indicates the input signal to one shot 85, appearing on lead 84, while reference numeral 94 indicates the output signal from one shot 85, as applied through switch 16 in a closed condition through loudspeaker 86. Pulse 91 of the return signal is passed by switch 80 during the gating interval through the input of one shot 85, and is of sufficient magnitude to trigger the one shot to change states. This occurs at time $t_2$, and one shot 85 remains in the set stage until $t_4$, which occurs in the preferred embodiment about 500 microseconds later.

Although a single pulse would provide only a single pulse or click at loudspeaker 86, it will be appreciate that the entire pulse transmission and reception cycle is repeated every millisecond, under control of the master timing pulses. Thus, assuming that a pregnancy condition is being detected, pulse 91 will be recurring at the input of the one shot at a one kilohertz rate, and the resulting one kilohertz output signal from the one shot will produce a continuous audible tone at the loudspeaker, so long as the probe is properly positioned on the animal from which data is being taken.

Referring again to FIG. 3, in which reference numeral 17 generally designates a sow being tested, the ultrasonic transducer 12 at the end of probe 11 is most advantageously place about two inches in front of the flank area and midway between the nipple line and the animal side body wall. For good ultrasonic pulse propagation, the end of the probe should be dipped in water, mineral oil or motor oil before placing it against the animals's abdomen.

Once the probe is in place, and the power switch 15 turned on, if a pregnancy condition is detected, the loudspeaker will automatically emit a tone. If no tone is present, and if probe placement is proper, either the sow is not pregnant or the gestation period is not sufficiently advanced.

Further data can be observed from the visual display on the face of CRT 14. In the trace shown in FIG. 3, the spike at the extreme left hand side corresponds to the initial transmitted pulse 23. Reference numeral 90 again designates a number of stronger returns from various internal parts of the animal at a shallower depth than the uterus. Reference numeral 71 designates the marker pulses which, as previously explained, deflect the beam downwardly. Since these pulses are spaced at approximately 80 microseconds, they correspond to depth increments of approximately 6 centimeters each. The gate is opened for a period from about 240 microseconds to about 320 microseconds following the original pulse, corresponding to a depth of about 24 to 30 centimeters. The strong return pulse 91 from the uterus is indicated by reference numeral 91. The sound can be defeated by turning off switch 16, if desired, but normally switch 16 would be left on with the audible tone providing the primary indication of pregnancy detection, and the visual display providing secondary information as previously explained.

While the above description of the preferred embodiment was given with respect to pregnancy detection in sows, it will be appreciated that the gating pulse duration and/or time delay in the present invention can be adjusted for different depths for detecting pregnancies or for detecting other body organs in various animals. The necessary timing changes can easily be effected by alteration of the frequency pulses provided by the marker generator 70, or by altering counter 75 to a divide by 3, divide by 5, etc. configuration, as may be necessary. Control of these variables can be provided by switchable circuits controlled from a front panel selector switch, so as to rapidly reprogram the device for a number of preselected applications.

The depth control 18 of FIG. 3 can be connected by suitable means to horizontal sweep generator 50 or horizontal amplifier 53, so as to spread horizontally the display on the cathode ray tube, to allow closer inspection thereof. This can be accomplished by modification of the horizontal sweep waveforms 51, by circuits well known in the prior art. Also, a sensitivity control 19 can be provided and connected by suitable means for adjusting the gain of signal amplifier 33 so as to allow closer study of various details of the waveform traces.

Thus, according to the present invention, there is provided an improved ultrasonic biological detection apparatus, including an automatic audible signalling device which generates the tone only when the expected return pulse of sufficient amplitude occurs in the defined time period corresponding to the predetermined depth zone in the animal.

What is claimed is:

1. Ultrasonic animal pregnancy detection apparatus with automatic audible pregnancy indication, comprising:
    (a) means for transmitting ultrasonic energy pulses and for receiving return pulses including a probe for placement on the body of the animal to be checked;
    (b) signal amplifier means for amplifying said pulses received by said transmitting and receiving means, said signal amplifier means having an amplification factor independent of the pulse propagation conditions within the animal's body;
    (c) means for generating a gating signal commencing after a predetermined time delay following the transmission of an ultrasonic energy pulse and continuing for a predetermined time interval, said time delay and time interval corresponding generally to the return pulse expected from the uterus of said animal;
    (d) means for generating an audible signal in response to an amplified return pulse of predetermined amplitude, said predetermined amplitude corresponding to the amplitude of a return pulse from an enlarged uterus indicating animal pregnancy; and
    (e) switching means for receiving said gating signal and for selectively transmitting amplified return pulses from said amplifier means to said audible signal generating means only during the time intervals defined by said gating signal, whereby the presence or absence of the expected return pulse is automatically audibly indicated.

2. Apparatus according to claim 1 wherein said means for generating a gating signal includes marker pulse generator means for generating a series of marker pulses after transmission of an ultrasonic energy pulse, and a counter means for receiving said marker pulses and for producing said gating signal after a predetermined number of marker pulses have been received.

3. Apparatus according to claim 2 wherein said counter means is further operable for discontinuing said gating signal after a predetermined further number of marker pulses have been received.

4. Apparatus according to claim 3 further including means for resetting said counter means upon each new transmission of an ultrasonic energy pulse to initiate a new measurement cycle.

5. Ultrasonic detection apparatus according to claim 1 further including timing means connected for initiating the transmitting of the ultrasonic energy pulses on a recurring basis at an audio frequency repetition rate, and wherein said audible signal generating means includes a loudspeaker so that the recurrence of amplified return pulses of predetermined amplitude within the time period of the gating signal causes said loudspeaker to produce an audible sound at said audio frequency.

6. Apparatus according to claim 5 wherein said audible signal generating means includes a pulse lengthening circuit connected to receive said amplified return pulses from said switching means and to deliver lengthened return pulses to said loudspeaker.

7. Apparatus according to claim 6 including means for establishing a threshold switching amplitude required to activate said pulse-lengthening circuit, whereby only amplified return pulses of a predetermined amplitude will be lengthened and passed to said loudspeaker.

8. Apparatus according to claim 6 wherein said pulse-lengthening circuit comprises a monostable multivibrator having an input connected from said switching means, and an output connected to said loudspeaker.

9. Apparatus according to claim 1 further comprising means including a cathode ray tube for displaying said amplified return pulses as a function of time.

10. The method of detecting and automatically indicating pregnancy in animals, comprising the steps of:
    transmitting ultrasonic energy pulses into the body of an animal to be checked by means of a probe placed on the animal's body;
    receiving return pulses from within the animal's body by means of said probe;
    amplifying received return pulses by an amplification factor independent of pulse propagation conditions within the animal's body;
    generating a time interval beginning a predetermined time delay after the transmission of a pulse and corresponding generally to the return pulse expected from the uterus of the animal;
    testing the amplitude of amplified return pulses occurring during said time interval against a predetermined amplitude corresponding to the return pulse from an enlarged uterus indicating pregnancy; and
    generating an audible tone when an amplified return pulse in said time interval equals or exceeds said predetermined amplitude, whereby to automatically audibly indicate detection of a pregnancy condition.

11. The method of claim 10 including the further steps of repeating said transmitting of ultrasonic energy pulses at an audio frequency repetition rate and applying amplified return pulses which occur in said time interval and which equal or exceed said predetermined amplitude to a loudspeaker to generate said audible tone.

* * * * *